United States Patent [19]

Johnson

[11] Patent Number: 5,152,763
[45] Date of Patent: Oct. 6, 1992

[54] METHOD FOR GRAFTING BONE

[76] Inventor: Lanny L. Johnson, 3800 Hagadorn Rd., Okemos, Mich. 48864

[21] Appl. No.: 679,190

[22] Filed: Apr. 2, 1991

[51] Int. Cl.⁵ .............................................. A61F 5/04
[52] U.S. Cl. ....................................................... 606/86
[58] Field of Search ................................ 128/749–755; 606/102, 86–94

[56] References Cited

U.S. PATENT DOCUMENTS

| | | | |
|---|---|---|---|
| 737,293 | 8/1903 | Summerfeldt . | |
| 2,543,780 | 3/1951 | Hipps et al. | 128/83 |
| 2,919,692 | 1/1960 | Ackermann | 128/754 |
| 3,147,749 | 9/1964 | Marsh | 128/751 |
| 3,682,177 | 8/1972 | Ames et al. | 606/172 |
| 3,848,601 | 11/1974 | Ma et al. | 606/61 |
| 4,010,737 | 3/1977 | Vilaghy et al. | 128/754 |
| 4,566,466 | 1/1986 | Ripple et al. | 606/102 |
| 4,782,833 | 11/1988 | Einhorn et al. | 606/80 |
| 4,877,020 | 10/1989 | Vich | 606/86 |
| 4,961,430 | 10/1990 | Sheahon | 128/754 |

FOREIGN PATENT DOCUMENTS 1319830  6/1987  U.S.S.R. .............................. 128/749

OTHER PUBLICATIONS

Stryker Surgical, United States Price List Effective Mar. 1, 1989.

Primary Examiner—C. Fred Rosenbaum
Assistant Examiner—M. Mendez
Attorney, Agent, or Firm—Cushman, Darby & Cushman

[57] ABSTRACT

An apparatus for manually securing a bone graft from a donor site and delivering the bone graft to an acceptor site includes a hollow cylindrical cutter and a solid inner cylindrical plunger. The cutter has a cutting end and a grasping end, with the cutting end being tapered to a sharp edge for cutting the bone graft from the donor site. The plunger is engageable with the hollow cutter to push the retained bore graft from the cutter into the acceptor site. Equidistantly spaced markings on the cutter and plunger can be used to gauge the depth of the bone graft.

1 Claim, 1 Drawing Sheet

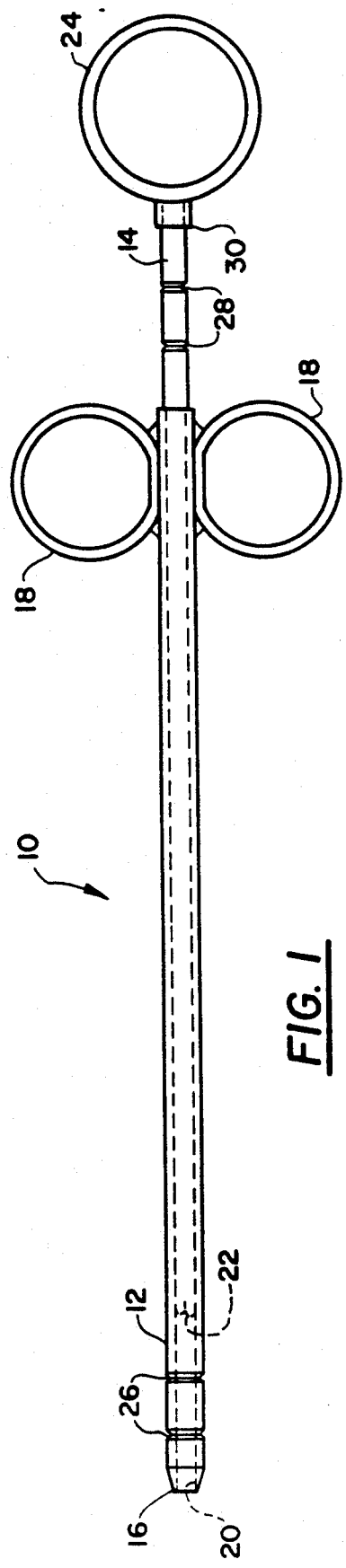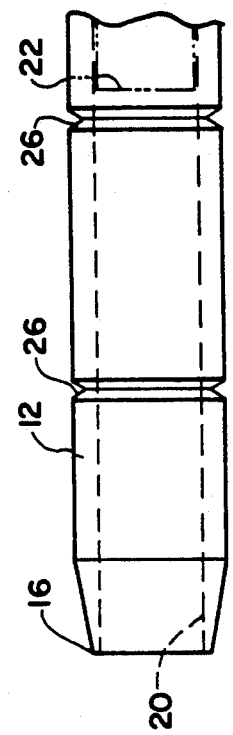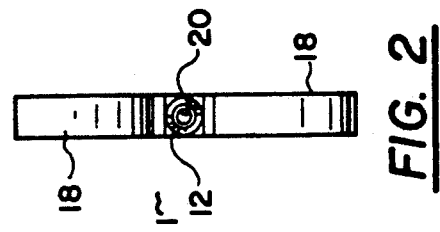

METHOD FOR GRAFTING BONE

BACKGROUND OF THE INVENTION

1. Field of the Invention

The present invention relates to an apparatus for securing and delivering a cancellous bone graft to an acceptor site.

2. Scope of the Related Art

In the field of orthopedic surgery, bone grafting is used to replace diseased or damaged bone with healthy bone from a donor site. While various manual and powered instruments are conventionally known for grafting bone, it is difficult to take properly shaped cylindrical bone grafts from a donor site and deliver the bone graft to the acceptor site, especially during arthroscopy. Further, it is desirable to be able to take and deliver the bone graft in a single operation.

SUMMARY OF THE PRESENT INVENTION

The preferred embodiment of the present invention provides a single, safe, effective hand instrument that secures a bone graft of cylindrical shape, and delivers the bone graft to the acceptor site in one operation. After delivery of the graft, the instrument may act as a bone graft impactor.

The bone grafter includes a hollow cylindrical cutter having a cutting end and a grasping end. The cutting end is tapered to a sharp edge for cutting the bone graft from the donor site. Two grasping handles attached to opposite sides of the grasping end provide a means by which the cutter can be manipulated to cut the bone graft from the donor site. When the desired depth of bone graft is achieved, the hollow cutter is angulated side to side to free the graft from the donor bone. The cut bone graft is retained in the hollow cylindrical cutter, whereby it can be delivered to the acceptor site which has already been prepared.

A solid inner cylindrical plunger having a pushing end and a grasping end is engageable with an interior of the hollow cylindrical cutter for pushing the retained bone graft into the acceptor site. Once the hollow cylindrical cutter and retained bone graft have been moved to the acceptor site, the plunger is pushed in, moving the bone graft out of the end of the hollow cutter and into the acceptor site. The empty bone grafter can then be removed and returned to the donor site for subsequent bone grafts, until the desired amount of graft has been placed.

With the foregoing in mind, other objects, features and advantages of the present invention will become apparent upon consideration of the following description and the appended claims with reference to the accompanying drawings, all of which form part of this specification, wherein like reference numerals designate corresponding parts in the various figures.

BRIEF DESCRIPTION OF THE DRAWINGS

FIG. 1 is a side elevational view of the bone grafter;

FIG. 2 is an end elevational view of the hollow cutter grasping end;

FIG. 3 is an enlarged partial view of the hollow cutter cutting end.

DETAILED DESCRIPTION OF THE PREFERRED EMBODIMENT

FIGS. 1-3 show a bone grafter 10 which includes a hollow cylindrical cutter 12 and a solid cylindrical plunger 14. The hollow cylindrical cutter 12 has a sharpened cutting edge 16 at a cutting end thereof and two grasping handles 18 attached to opposite sides of a grasping end of the cutter 12. The cutter 12 further includes a longitudinal through-bore 20 having a diameter slightly greater than a diameter of a pushing end 22 of the solid cylindrical plunger 14 so that the solid cylindrical plunger 14 can be inserted into the through-bore 20 of the hollow cutter 12. The solid plunger 14 also has an attached grasping handle 24 for manipulating the plunger 14 with relation to the cutter 12.

The cutter 12 has a plurality of markings 26 equidistantly spaced from the cutting edge 16. Similarly, the plunger 14 has a plurality of markings 28 equidistantly spaced from a bottoming ridge 30. In the preferred embodiment, the first cutter marking 26 is spaced 1 cm from the cutting edge 16 with each subsequent marking 26 spaced an additional 1 cm from the cutting edge 16 and the first plunger marking 28 is spaced 1 cm from the bottoming ridge 30 with each subsequent marking 28 spaced an additional 1 cm from the bottoming ridge 30. In alternative embodiments, the spacing can be varied as desired. When the plunger 14 is inserted fully into the cutter 12 until the bottoming ridge 30 contacts the cutter 12, the pushing end 22 of the plunger 14 is flush with the cutting edge 16. Therefore, these equidistantly spaced markings 26 and 28 can be used to determine the depth and placement of the bone graft.

To use the bone grafter 10, the bone graft donor site is surgically exposed. The compact design of the bone grafter allows the donor site to be approached through a small incision in the soft tissue and via a drill hole in the bone cortex. A large formal incision is not necessary as with many conventional bone grafting apparatuses.

The surgeon then determines the desired diameter and depth of the bone graft. The bone grafter 10 can be constructed in any desired size, although the most common embodiment will be dimensioned to remove 4 mm or 8 mm diameter bone grafts, respectively, as determined by the diameter of the through-bore 20. After the surgeon has determined the appropriate diameter of bone graft necessary, the depth of the bone graft is determined by placing the cutting end of the bone grafter into the acceptor defect and gauging the depth by means of the cutter markings 26.

The plunger 14 is then retracted from the cutter 16 by this depth using markings 28 as a gauge and the bone grafter 10 with the retracted plunger 14 is pushed into the donor cancellous bone to the desired depth. When this desired depth is achieved, using markings 26 as a gauge, the instrument is angulated side to side to free the graft from the donor bone. The bone grafter 10 and retained bone graft can then be removed from the donor site and moved to the acceptor site.

The cutting edge 16 is placed at the exact site of deposition and the plunger 14 is pushed in, moving the bone graft out of the hollow cutter 12 into the acceptor site. Slight retraction of the hollow cutter 12 during delivery causes less impaction of the bone graft while greater impaction can be obtained by holding the hollow cutter 12 firm during delivery. The bone grafter 10 can be used as an impactor if the plunger 14 is fully inserted into the cutter 12. The empty bone grafter 10 is then removed and returned to the donor cancellous bone for subsequent grafts, until the desired amount of bone graft has been placed.

Further, if cancellous bone, which is soft and sparse, is used for the bone graft, it may be desirable to first compact the bone prior to placement. For instance, a 2 cm graft can be harvested with the bone grafter, as discussed above. The bone graft can be compacted to 1 cm by compressing the bone graft between the plunger 14 and a solid sterile surface placed against the end of the bone grafter 10. The compressed bone graft can then be delivered to a 1 cm acceptor site as discussed above. This increases the density of the graft for a mechanically stronger graft.

In the preferred embodiment, the bone grafter 10 is constructed of stainless steel, although any appropriate metal or other material or combination of materials could be used. The grasping handles 18 and 24 are metal rings which are silver soldered to the cutter 12 and plunger 14, respectively. However, any appropriate means of attachment could be used. The overall length of the cutter 12 is approximately 18 cm. The markings 26 and 28 can be cut into the cutter 12 and plunger 14, engraved, printed or provided in any known manner.

While the invention has been described in accordance with what is presently conceived to be the most practical and preferred embodiment, it is to be understood that the invention is not to be limited to the disclosed embodiment but on the contrary, is intended to cover various modifications and equivalent arrangements included within the spirit and the scope of the appended claims, which scope is to be accorded the broadest interpretation of such claims so as to encompass all such equivalent structures.

I claim:

1. A method for grafting bone, comprising the steps of:

surgically preparing a bone acceptor site;

surgically exposing a bone donor site;

determining a desired diameter of bone graft;

determining a desired depth of bone graft by placing a cutting end of a bone grafter into an acceptor defect and gauging the depth by means of equidistantly spaced markings on an exterior of the bone grafter;

retracting a plunger from the bone grafter by a distance greater than the desired depth of bone graft, using equidistantly spaced markings on an exterior of the plunger as a guide;

pushing a sharpened cutting end of the bone grafter into the donor bone site to the desired depth while maintaining the plunger in the retracted state;

angulating the bone grafter side to side to free the bone graft after the desired depth has been achieved;

compacting the bone graft to the desired depth by compressing the bone graft between a flat end of the plunger and an additional surface;

moving the bone grafter and retained bone graft to the acceptor site;

placing the cutting edge of the bone grafter at the exact site of deposition;

pushing the plunger into the bone grafter to move the bone graft out of the bone graft and into the acceptor site; and removing the bone grafter from the acceptor site.

* * * * *